United States Patent [19]

Shestock

[11] Patent Number: 5,774,209
[45] Date of Patent: Jun. 30, 1998

[54] TRANSMITTANCE CELL FOR SPECTROPHOTOMETER

[75] Inventor: Michael A. Shestock, Rush, N.Y.

[73] Assignee: Spectronic Instruments, Inc., Rochester, N.Y.

[21] Appl. No.: 728,298

[22] Filed: Oct. 8, 1996

[51] Int. Cl.[6] ............................. G01N 21/01; G01N 21/13
[52] U.S. Cl. .............................. 356/73; 356/328; 356/440; 356/244
[58] Field of Search .................... 356/328, 440, 356/244, 73

[56] References Cited

U.S. PATENT DOCUMENTS

| | | | |
|---|---|---|---|
| 2,864,279 | 12/1958 | Phifer | 356/244 |
| 3,762,817 | 10/1973 | Harklau | 356/73 |
| 3,923,399 | 12/1975 | Brumley | 356/328 |
| 3,958,882 | 5/1976 | Gast | 356/73 |
| 3,977,787 | 8/1976 | Fletcher et al. | 356/244 X |
| 3,977,794 | 8/1976 | Liedholz | 356/244 |
| 4,012,144 | 3/1977 | Hedelman | 356/73 |
| 4,029,419 | 6/1977 | Schumann, Jr. et al. | 250/266 X |
| 4,171,909 | 10/1979 | Kramer et al. | 356/73 |
| 4,669,873 | 6/1987 | Wirz | 356/328 X |
| 4,682,890 | 7/1987 | de Macario et al. | 356/244 |
| 4,760,258 | 7/1988 | Gast et al. | |
| 4,886,355 | 12/1989 | Keane | 356/328 X |
| 4,886,366 | 12/1989 | Kogure | 356/406 |
| 5,153,675 | 10/1992 | Beauchaine | 356/244 X |
| 5,325,181 | 6/1994 | Wilman | 356/448 |

FOREIGN PATENT DOCUMENTS

| | | | |
|---|---|---|---|
| 399057 | 11/1990 | European Pat. Off. | 356/328 |
| 2249389 | 5/1992 | United Kingdom | 356/328 |

*Primary Examiner*—Vincent P. McGraw
*Attorney, Agent, or Firm*—Neal L. Slifkin

[57] ABSTRACT

A hand-held portable spectrophotometer that is contained in an enclosed housing and includes a source of illumination and a spectrograph, along with a transmittance cell and a reflectance cell. The transmittance cell is adapted to receive therein either a solid sample or a liquid sample through an access door in the top wall of the housing.

18 Claims, 5 Drawing Sheets

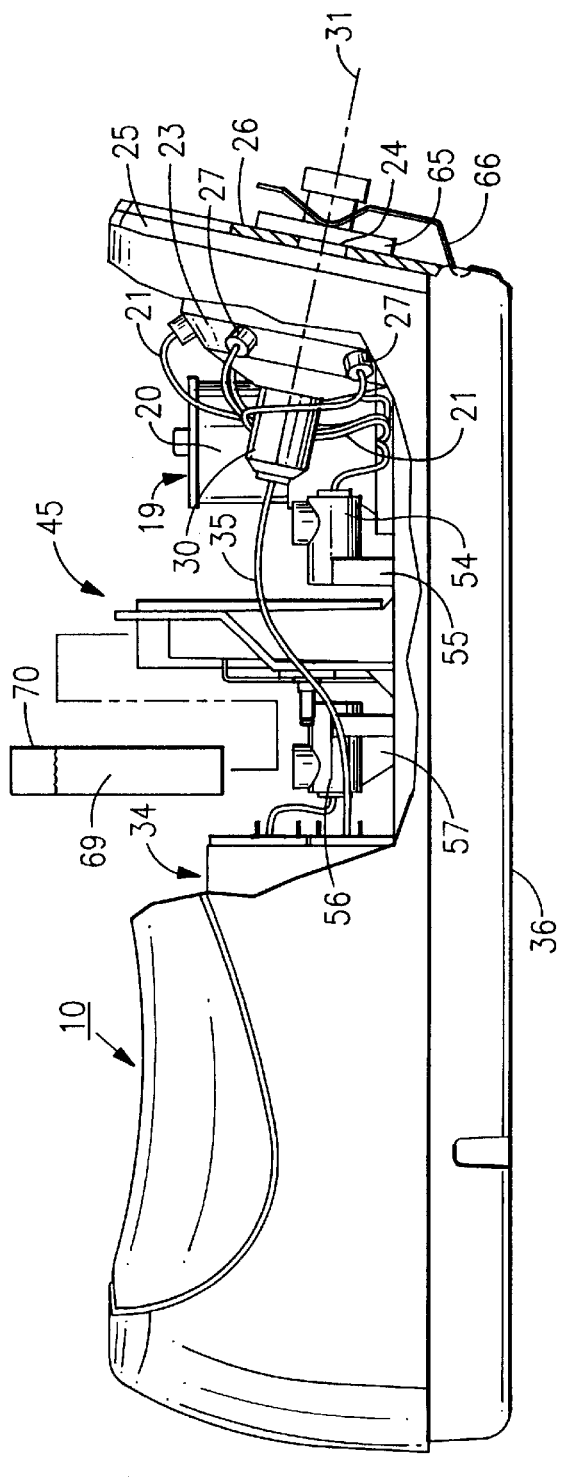
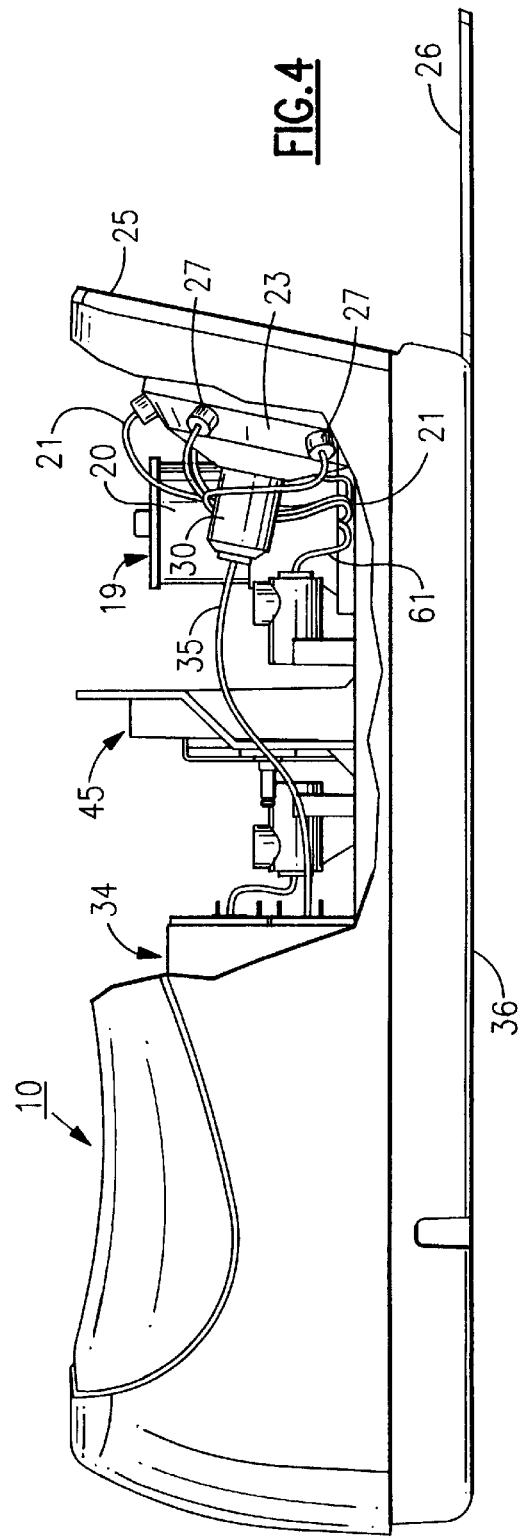

TRANSMITTANCE CELL FOR SPECTROPHOTOMETER

BACKGROUND OF THE INVENTION

This invention relates to a spectrophotometer or colorimeter and, in particular, to a portable hand-held spectrophotometer capable of analyzing either the reflectance or the transmittance from a sample target. More specifically, this invention relates to a transmittance cell for selectively mounting either a solid or a liquid light transmitting sample target in a hand-held spectrophotometer.

Although portable spectrophotometers are known in the art, these instruments typically provide only one mode of operation, that is, either a reflectance mode of operation or a transmittance mode of operation. Although these instruments are portable, they nevertheless are generally not small enough to be hand-held and thus, are difficult to use in the field. In addition, the portable instruments found in the prior art that are adapted to perform color measurement on translucent samples cannot handle both liquid samples and solid samples, and as a result, have limited value to the user.

SUMMARY OF THE INVENTION

It is an object of the present invention to improve spectrophotometers.

It is a further object of the present invention to provide a compact, portable hand-held spectrophotometers.

A still further object of the present invention is to provide a hand-held spectrophotometer that is capable of performing color measurements on either reflectance samples or transmittance samples.

Another object of the present invention is to provide a transmittance cell for a hand-hold spectrophotometer that is capable of handling both solid and liquid transmittance samples.

These and other objects of the present invention are attained by means of a hand-held portable spectrophotometer that includes a compact housing containing a source of illumination and a spectrograph for analyzing light images provided by either a reflectance sample or a transmittance sample. A transmittance cell that is capable of supporting either a solid or a liquid sample is mounted within the housing. Light from the illumination source is brought into a first optical housing located at the entrance to the transmittance cell wherein the light is collimated and directed through the cell along a defined optical axis. The light beam passing through the cell is received in a second optical housing and focussed upon a fiber bundle which transmits the light to the spectrograph for analyzing. A guide is contained in the transmittance cell for slidably receiving therein a solid transmittance sample in the form of a flat plate and aligning the sample in the light beam. A liquid sample holder is removably mountable in the transmittance cell so that the light beam passes through a liquid sample contained in the holder. Access to the transmittance cell is provided by an access door mounted in the top wall of the hand-held housing through which either solid or liquid transmittance samples can be loaded into or unloaded out of the transmittance cell.

BRIEF DESCRIPTION OF THE DRAWINGS

For a better understanding of these and other objects of the present invention reference shall be made to the following detailed description of the invention which is to be read in association with the accompanying drawings, wherein:

FIG. 3 is a side elevation of the spectrophotometer shown in FIG. 2 with portions broken away illustrating the instrument in the transmittance mode of operation;

FIG. 4 is a side of the spectrophotometer shown in FIG. 2 with portions broken away illustrating the instrument in the reflectance mode of operation;

DESCRIPTION OF THE INVENTION

Figure 1:
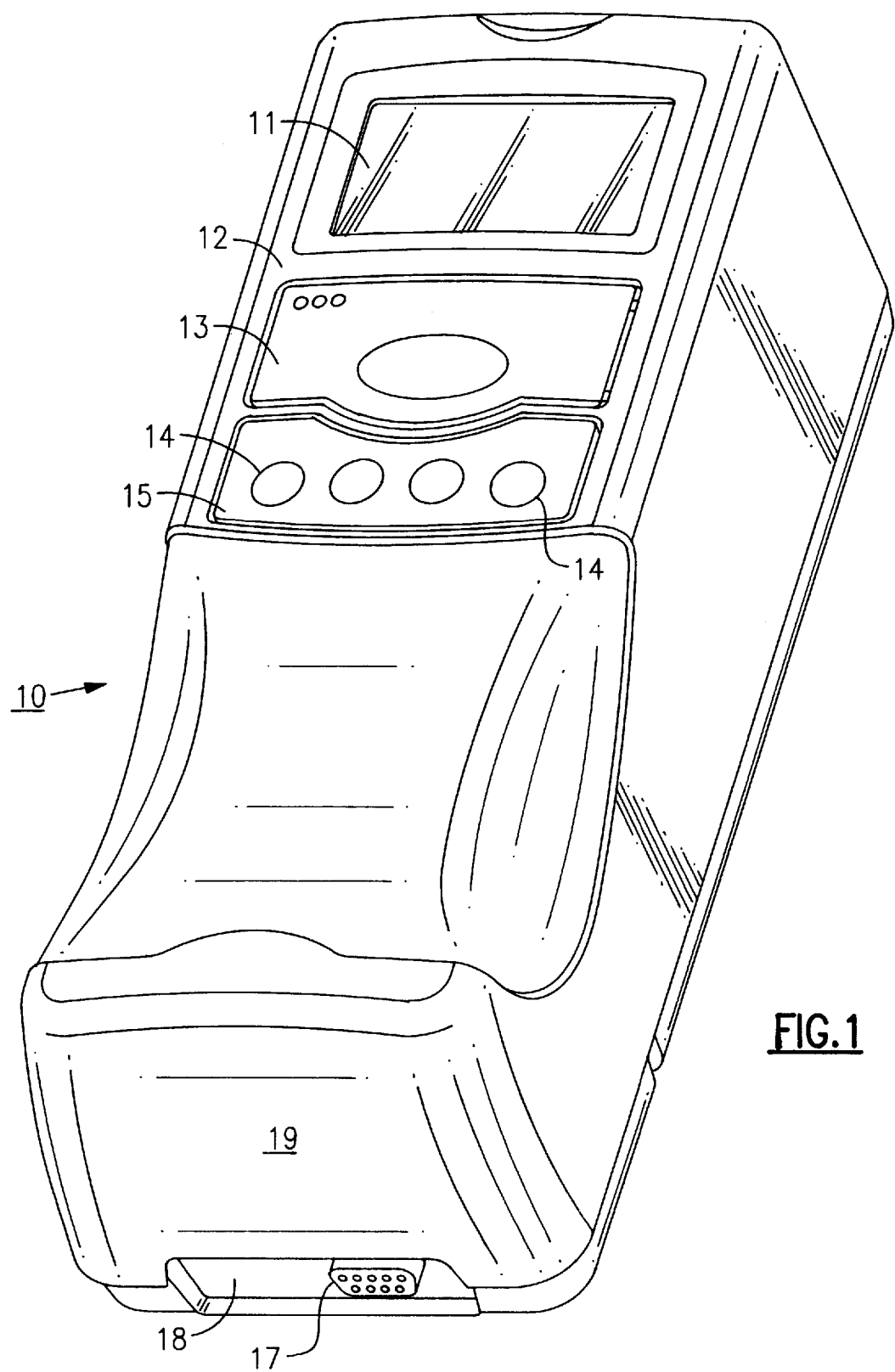
FIG. 1 is a perspective view of a hand-held portable spectrophotometer embodying the teachings of the present invention.

Referring initially to FIG. 1, there is shown a rectangular shaped hand-held housing, generally referenced 10, containing a battery operated spectrophotometer embodying the teachings of the present invention. The housing contains a readout window 11 located in top wall 12 which provides visual data to the user relating to the operation of the instrument and color information relating to either a reflectance or transmittance sample that has been analyzed by the instrument. Immediately behind the readout window is an access door 13 that can be opened to provide ready access to a transmittance cell located directly beneath the door inside the housing. As will be explained in greater detail below, the transmittance cell is adapted to hold either a solid or a liquid sample. A series of control switches 14—14 are located in a control panel 15 mounted in the top wall of the housing behind the access door.

A pin connector 17 is mounted in a recess 18 provided in the back wall 19 of the housing which allows the housing to be connected directly into a docking station located in a computer (not shown). When docked in the computer, the battery is disconnected and power is provided to the spectrophotometer from the computer thus preserving the battery. Communication is also established between the spectrograph mounted in the housing and the computer circuits which includes programs for further expanding the functionality of the instrument. When docked in the computer, the spectrophotometer is still able to operate in both the reflectance mode and transmittance mode to analyze a wide range of solid and liquid samples.

Turning now to FIGS. 2–6, there is shown the hand-held instrument with its top cover removed or broken away to better see the internal components of the instrument. Mounted inside the housing is an illumination source generally referenced 19. A high intensity source of white light is contained within a light housing 20. Fiber bundles 21—21 carry light from the source to a cup shaped support block 23 mounted on the front wall 25 of the housing. A cover 26 is hinged to the front wall of the housing which contains a viewing orifice 24 through which a target is viewed by the instrument. The support block and the front wall of the housing, and its cover, combine to form what will herein be referred to as a reflectance cell. Light ports 27—27 are mounted at 60° intervals about the support block and are coupled to the source of illumination by the above mentioned fiber bundles 21—21. The ports are arranged to direct multiple beams of illumination at the viewing orifice to illuminate the target area. A reflected light image of the target area is transmitted back to a viewing lens system 30 of the support block along the image axis 31. The image is transmitted back to a spectrograph 34 located in the back of the housing by a reflectance fiber bundle 35.

As illustrated in FIG. 4, the cover 26 is hinged to the housing so that it can pivot downward into the plane described by the bottom surface 36 of the housing. Accordingly, the viewing orifice can he accurately placed over a desired target when the cover is in a down position. Once the target is framed in the viewing orifice, the housing is closed against the cover and the sample read.

Figure 2:
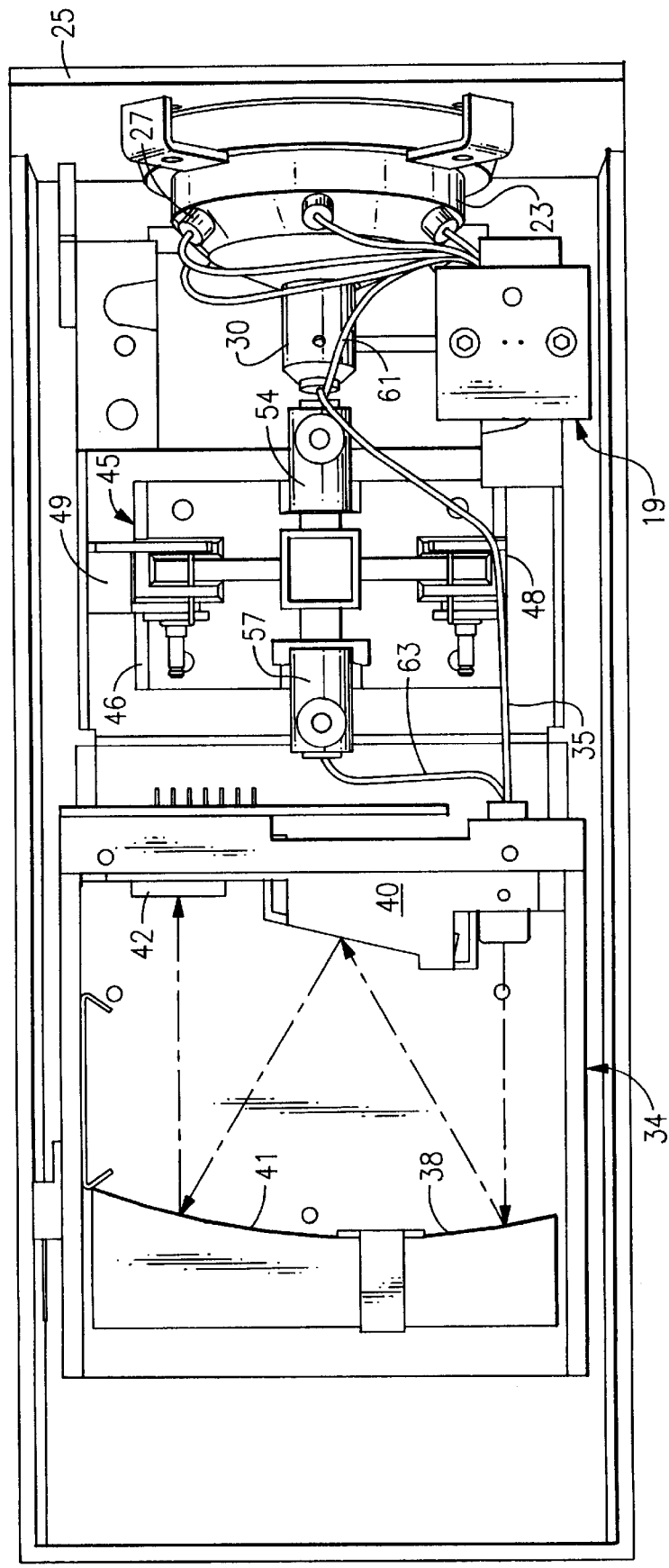
FIG. 2 is a top view of the hand-held spectrophotometer shown in FIG. 1 with the covers removed to more clearly show the component parts of the instrument.

As best seen in FIG. 2, the reflected light image entering the spectrograph is directed at a first mirror surface 38 which reflects the image back onto a diffraction grating 40 which separates the image into its spectral color components. The separated image data, in turn, is directed onto a second mirror surface 41 and then onto a photodetector 42. The photodetector is connected to a suitable circuitry for analyzing the color distribution data and displaying the results of the analysis in the read out window 11 of the housing.

Figure 5:
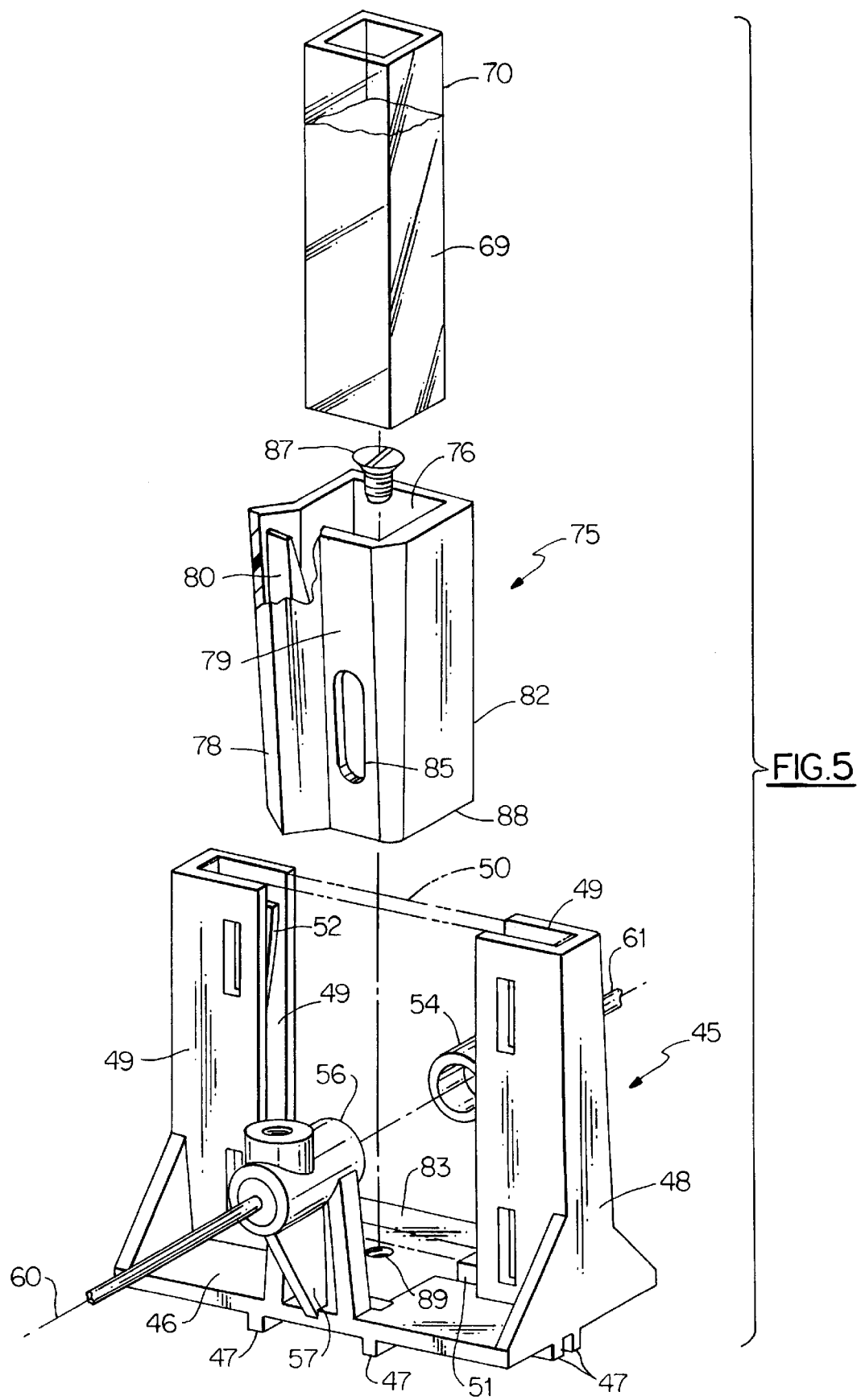
FIG. 5 is an enlarged exploded view in perspective of the transmittance cell contained within the hand-held instrument for mounting either a solid or a liquid sample in the instrument.
Figure 6:
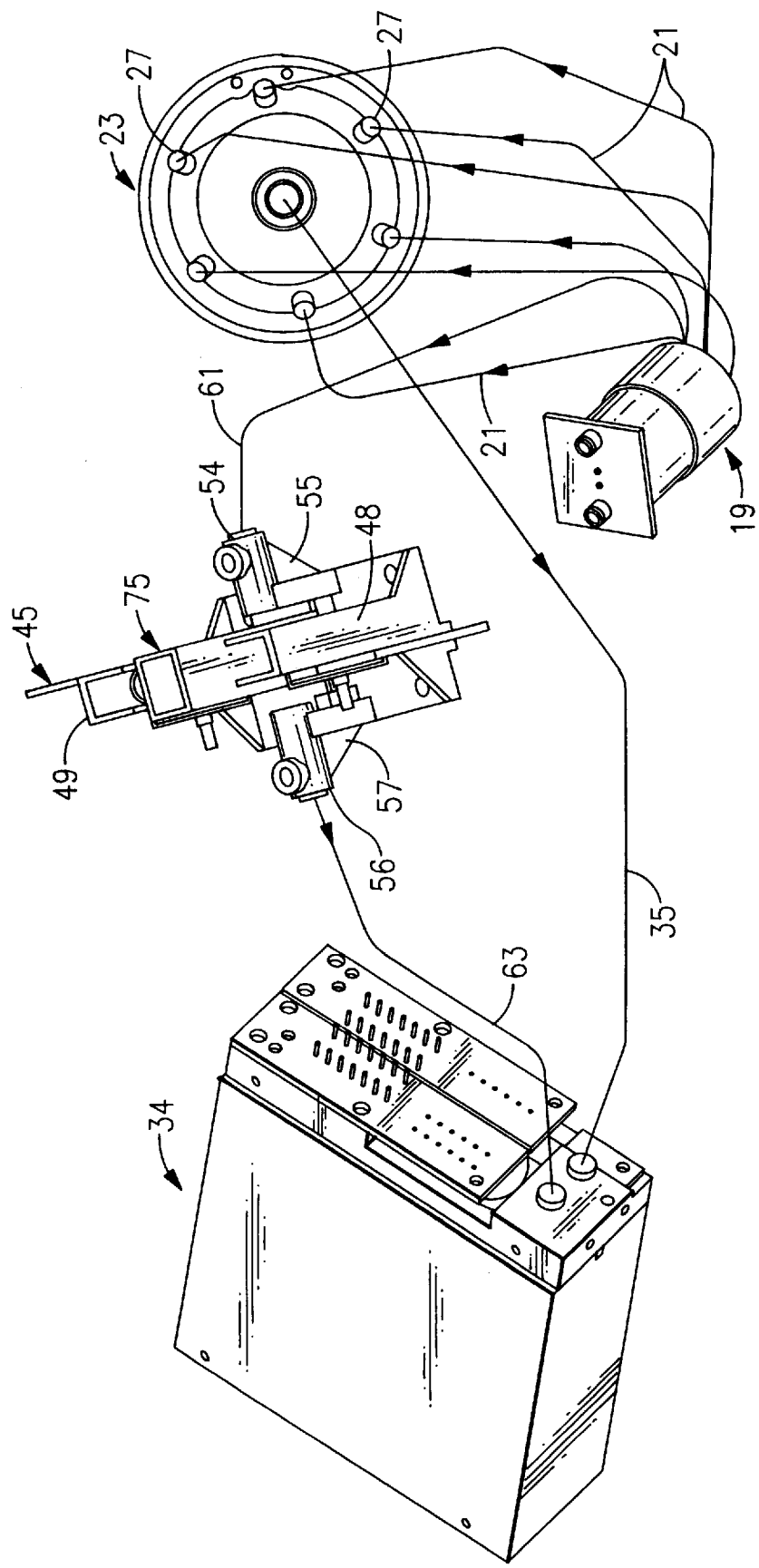
FIG. 6 is a schematic view in perspective showing the fiber optic light paths through the instrument.

As noted above, a transmittance cell 45 is mounted behind the remittance cell inside the housing. As illustrated in FIG. 5, the transmittance cell includes a base plate 46 that is seated upon the bottom wall of the housing upon legs 47 and secured in place beneath the access door by threaded fasteners (not shown). A pair of spaced apart columns 48 and 49 are mounted in an upright position on either side of the base plate. Each column contains a recessed guideway 49. As shown in phantom outline, a flat solid sample 50 is slidably received in the guideway so that it can be passed downwardly into contact with indexing pads 51 which are carried on the base plate. A leaf spring 52 is mounted inside one of the guideways to bias the sample into contact against the back wall of the guideway. The solid sample is readily loaded into the cell through the access door located in the top wall of the housing.

A first optical housing 54 is mounted upon a raised stanchion 55 at one end or the base plate. A second optical housing 56 is similarly mounted upon another stanchion 57 at the opposite end of the base plate. The two housings are coaxially aligned along an optical axis 60 that passes between the two upraised columns 48 and 49.

Preferably, the base plate, raised channel members, optical housing, and stanchions are all integrally molded or otherwise formed from a simple piece of material such as a high strength plastic.

A light input fiber bundle 61 is arranged to bring white light from the illumination source into the first optical housing. An optical lens system is mounted within the housing for collimating the light and directing a collimated beam of light along the optical axis. The second optical housing contains a second lens system for focussing the incoming light upon the light entrance face of a light output fiber bundle 63. The output bundle is arranged to bring the light to a second input to the spectrograph. Here again, the entering light is directed along the light path shown in FIG. 2 to the diffraction grating and then onto a second photodetector.

Placing the spectrophotometer in the reflectance mode of operation programs the instrument to analyze the color content of a target mounted in the viewing orifice of the reflectance cell. At this time, the transmittance cell does not contain a target and undisturbed white light from the illumination source is passed through the transmittance cell to the spectrograph where it is used as a reference signal in the analyzer. Placing the spectrophotometer in the transmittance mode of operation programs the instrument to analyze the color content of a transmittance target mounted in the transmittance cell. As illustrated in FIG. 3, a white card or tile 65 is mounted over the viewing orifice in the cover and held tightly thereagainst by means of a spring loaded clamp 66. The white card image is transmitted via fiber bundle 35 to the spectrograph and is now used as the reference signal. A transmittance target, such as liquid containing curvette or vile 70, is placed in the transmittance cell within the collimated light beam and the light passing through the target is transmitted via fiber bundle 35 to the spectrograph where it is analyzed.

The transmittance cell is adapted to receive therein both solid translucent samples, such as the plate 50 shown in FIG. 5, and a liquid sample 69 contained in a rectangular curvette or vile 70. The vile is adapted to pass downwardly into a rectangular shaped curvette 75 having a complimentary opening 76 formed therein. A close sliding fit is provided between the vile and the opening whereby the vile fits snugly within the cuvette. A spring chamber 78 runs axially along the back wall 79 of the cuvette holder. The chamber opens into the cuvette opening 76 and contains a spring 80 for frictionally holding the vile in the cuvette holder. The spring biases the vile into contact with the front wall 82 of the cuvette holder to properly align the vile in the cuvette holder.

The cuvette holder is arranged to fit into a recess 83 formed in the top surface of the base plate so that the front wall of the cuvette holder is perpendicularly aligned within the light beam passing through the cell. A pair of elongated slotted openings 85 are contained in the front and back walls of the cuvette holder that permit the light beam to pass into and out of the cuvette holder without being disturbed by the cuvette holder structure. The cuvette is capable of passing through the access door opening in the top wall of the housing and being positioned in the recess in the base plate. A screw 87 is rotatably contained in the bottom wall 88 of the cuvette holder which is threaded into a hole 89 in the base plate to secure the cuvette holder to the base plate. When the cuvette holder is positioned in the transmittance cell, viles containing various liquid samples can be easily inserted and removed from the cuvette holder through the access door.

The cuvette holder, in the preferred embodiment of the invention, is removably mounted in the transmittance cell between the two solid sample support columns to save space. However, the cuvette holder can be permanently mounted in the base plate to one side or the other of the columns without departing from the teachings of the present invention. By offsetting mounting of the cuvette holder in the base plate, the present instrument can more rapidly be converted for use when analyzing both solid and liquid transmittance samples.

While this invention has been explained with reference to the structure disclosed herein, it is not confined to the details set forth and this invention is intended to cover any modifications and changes as may come within the scope of the following claims:

What is claimed is:

1. Apparatus for mounting either a solid translucent sample or a liquid sample in a spectrophotometer that includes, a base plate, a pair of opposed spaced apart columns mounted upon the base plate having guide means for slidably receiving therein a solid translucent sample, first and second opposed optical housings mounted on said base plate that are spaced apart along an optical axis that passes between said columns, said first optical housing containing first optical means for directing a light beam along said optical axis, said second optical housing containing second optical means for receiving light from said first optical housing and transmitting said light to a spectrograph for analysis, a cuvette holder mounted in said base plate between said optical housings, said cuvette holder containing window means therein for permitting said light beam to pass undisturbed through said cuvette holder, and a transparent vile for holding a liquid sample that is removably contained within said cuvette holder to position said liquid sample in said light beam.

2. The apparatus of claim 1 wherein said vile has flat parallel front and rear walls that are perpendicularly aligned with said light beam when said vile is contained in said cuvette holder.

3. The apparatus of claim 1 wherein said base plate, said columns and said optical housings are integrally formed from a single piece of material.

4. The apparatus of claim 1 wherein said first optical means further includes an input fiber bundle for introducing light from said source of illumination into said first optical housing and means for collimating said light.

5. The apparatus of claim 4 wherein said second optical means further includes an output fiber bundle for transmitting light to the spectrograph and means for focussing the light beam onto a light entrance face of said output fiber bundle.

6. The apparatus of claim 1 that further includes fastening means for removably securing the cuvette holder to said base plate.

7. The apparatus of claim 6 that further includes positioning means to align said cuvette holder in said base plate.

8. The apparatus of claim 1 wherein each opposed columns has a recess formed therein for slidably receiving a flat solid sample between said columns.

9. The apparatus of claim 8 that further includes biasing means associated with at least one of said columns for urging said flat solid sample received in said recesses against indexing surfaces located on said recesses to perpendicularly align said flat sample with said optical axis.

10. The apparatus of claim 1 wherein said vile is rectangular in form and is arranged to be slidably received in a complementary opening passing downwardly through the top of said cuvette holder.

11. The apparatus of claim 10 that further includes an indexing means for positioning the vile in said cuvette holder so that front and rear walls of said vile are perpendicularly aligned with said optical axis.

12. A portable spectrophotometer that is contained within a hand-held housing having end walls, opposed sidewalls and top and bottom walls, said housing further containing a source of illumination;

a spectrograph for analyzing light from a sample and determining the color content of said sample, a transmittance cell in which transmittance samples to be analyzed for color content are mounted, a first optical housing for directing a light beam from said source of illumination along an optical axis through said transmittance cell, a second optical housing for receiving light that has passed through said transmittance cell and delivering said light to said spectrograph, guide means in said cell for mounting a solid translucent sample therein and positioning said solid sample in the said light beam, a transparent liquid sample holder is removably contained in said cell for mounting a liquid sample in said light beam, and an access door in said top wall of the housing through which transparent liquid samples and solid translucent samples are passed into and out of said transmittance cell.

13. The portable spectrophotometer of claim 12 wherein said transparent liquid sample holder is a rectangular shaped vile and further includes a cuvette holder located in said transmittance cell for mounting said vile in said light beam.

14. The portable spectrophotometer of claim 13 wherein said cuvette holder contains clear windows for allowing the light beam to pass through said cuvette holder whereby the light beam is undisturbed by said windows.

15. The portable spectrophotometer of claim 12 wherein said first optical housing contains means for collimating the light that passes through said first optical housing.

16. The portable spectrophotometer of claim 15 wherein said second optical housing is connected to the spectrograph by a fiber bundle and said second optical housing contains lens means for focussing said light beam and entrance face to said fiber bundle.

17. The portable spectrophotometer of claim 12 wherein said guide means includes a pair of upright spaced apart columns positioned on either side of said optical axis having recesses formed therein for slidably receiving a flat solid sample therein and positioning said sample so that it is perpendicularly aligned with said optical axis.

18. The portable spectrophotometer of claim 17 wherein said cuvette holder is removably mounted in said transmittance cell between said columns.

* * * * *